(12) United States Patent
Peitz

(10) Patent No.: US 8,889,353 B2
(45) Date of Patent: Nov. 18, 2014

(54) METHOD FOR MONITORING THE BISULFITE-MEDIATED CONVERSION OF DNA

(75) Inventor: Ingmar Peitz, Emmendingen (DE)

(73) Assignee: Koninklijke Philips N.V., Eindhoven (NL)

( * ) Notice: Subject to any disclaimer, the term of this patent is extended or adjusted under 35 U.S.C. 154(b) by 190 days.

(21) Appl. No.: 13/497,065

(22) PCT Filed: Sep. 15, 2010

(86) PCT No.: PCT/IB2010/054163
§ 371 (c)(1),
(2), (4) Date: Mar. 20, 2012

(87) PCT Pub. No.: WO2011/036609
PCT Pub. Date: Mar. 31, 2011

(65) Prior Publication Data
US 2012/0171691 A1    Jul. 5, 2012

(30) Foreign Application Priority Data

Sep. 23, 2009   (EP) .................................... 09171053

(51) Int. Cl.
*C07H 21/04*     (2006.01)
*C12Q 1/68*     (2006.01)
(52) U.S. Cl.
CPC ........ *C12Q 1/6827* (2013.01); *C12Q 2523/125* (2013.01); *C12Q 2565/30* (2013.01); *C12Q 2521/531* (2013.01)
USPC ........................... 435/6.1; 435/91.1; 435/91.2
(58) Field of Classification Search
CPC ........... C12Q 1/6827; C12Q 2521/531; C12Q 2523/125; C12Q 2565/30

USPC ......................................................... 435/6.1
See application file for complete search history.

(56) References Cited

U.S. PATENT DOCUMENTS

| | | | |
|---|---|---|---|
| 5,952,176 | A | 9/1999 | McCarthy et al. |
| 7,175,982 | B1 | 2/2007 | McCarthy et al. |
| 2005/0202490 | A1 | 9/2005 | Makarov et al. |
| 2008/0311627 | A1 | 12/2008 | Tetzner et al. |
| 2009/0233804 | A1* | 9/2009 | Kurn et al. ......................... 506/9 |

FOREIGN PATENT DOCUMENTS

WO    2008149237    12/2008

OTHER PUBLICATIONS

Kubareva et al. (Biotecuniques, vol. 33, No. 3, pp. 526-531, Sep. 1, 2002).*
G.G. Wilson and N.E. Murray (1991), Annu. Rev. Genet. 25, pp. 585-627.
E. Li (2002), Annu. Rev. Genet. 3, pp. 662-673.
K.D. Robertson and A.P. Wolffe (2002), Nat. Rev. Genet. 1, pp. 11-19.

(Continued)

*Primary Examiner* — Jeanine A Goldberg

(57) ABSTRACT

The present invention relates to a method for monitoring the progression of the bisulfite-mediated conversion of DNA during DNA methylation analysis. The method is based on the reaction of the enzyme uracil-DNA-glycosylase (UNG) with at least one labeled DNA reporter molecule, the reporter molecule comprising at least one unmethylated cytosine residue in its sequence. After bisulfite-mediated conversion of unmethylated cytosine residues in uridin residues UNG removes the uracil bases from the DNA backbone, thus making it susceptible to heat-induced hydrolytic cleavage. Finally, the labels released from the DNA reporter molecule during this fragmentation process are detected.

16 Claims, 6 Drawing Sheets

(56) References Cited

OTHER PUBLICATIONS

A.P. Bird (2002), Genes Dev. 16, pp. 6-21.
T. Rein, et al. (1998), Nucleic Acids res. 26, pp. 2255-2264.
J. Sambrook, et al., (1989), Molecular, Cloning: A Laboratory Manual, 2nd ed., Cold Spring Harbor Laboratory Press, Cold Spring Harbor, NY.
F. Lottspeich and H. Zorbas (1998), Bioanalytic, Spektrum Akademischer Verlad, Heidelberg/Berlin, Germany.
B. Liu, et al., (2005), Proc. Natl. Acad. Sci. USA 102, pp. 589-593.
Y. Xu, et al., (1999), Proc. Natl. Acad. Sci., USA 96, pp. 151-156.
A.A. Sartori, et al., (2001), J. Biol. Chem. 276, pp. 29979-29986.
A.A. Sartori, et al., (2002) EMBO J. 21, pp. 3182-3191.
E.A. Kubareva, et al., Determination of Methylation Site of DNA-Methyltransferase NIaX by a Hybrid Method, BioTechniques 33, Sep. 2002, pp. 526-531.
Y Wang, et al., "In SituBisulfite Modification of Membrane-Immobilized DNA for Multiple Methylation Analysis", ScienceDirect, Analytical Biochemistry 359 (2006), pp. 183-188.

* cited by examiner

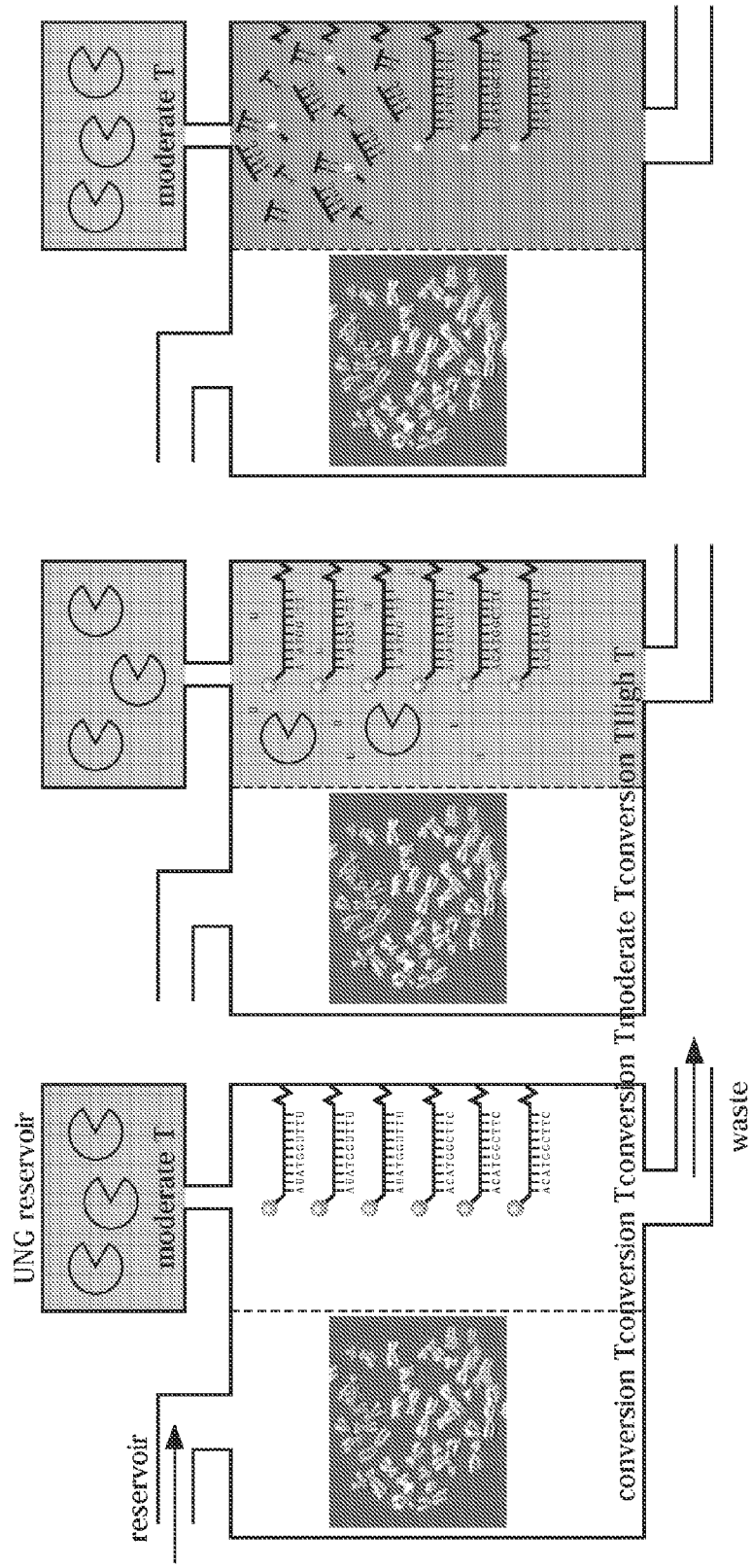

METHOD FOR MONITORING THE BISULFITE-MEDIATED CONVERSION OF DNA

FIELD OF THE INVENTION

The present invention relates to a method for monitoring the progression of the bisulfite-mediated conversion of DNA during DNA methylation analysis. The method is based on the reaction of the enzyme uracil-DNA-glycosylase (UNG) with at least one labeled DNA reporter molecule, the reporter molecule comprising at least one unmethylated cytosine residue in its sequence. After bisulfite-mediated conversion of unmethylated cytosine residues in uridin residues UNG removes the uracil bases from the DNA backbone, thus making it susceptible to heat-induced hydrolytic cleavage. Finally, the labels released from the DNA reporter molecule during this fragmentation process are detected.

Uracil-DNA-glycosylase and uracil-N-glycosylase, abbreviated sometimes as UNG or UDG are to be understood as being similar or synonymous. In any case, the terms are used in this application to indicate the enzyme making the DNA backbone susceptible to heat-induced hydrolytic cleavage.

BACKGROUND OF THE INVENTION

DNA methylation is found in the genomes of diverse organisms including both prokaryotes and eukaryotes. In prokaryotes, DNA methylation occurs on both cytosine and adenine bases and encompasses part of the host restriction system. In multicellular eukaryotes, however, methylation seems to be confined to cytosine bases and is associated with a repressed chromatin state and inhibition of gene expression (reviewed, for example, in Wilson, G. G. and Murray, N. E. (1991) *Annu. Rev. Genet.* 25, 585-627).

In mammalian cells, DNA methylation predominantly occurs at CpG dinucleotides, which are distributed unevenly and are underrepresented in the genome. Clusters of usually unmethylated CpGs (referred to as CpG islands) are found in many promoter regions (reviewed, e.g., in Li, E. (2002) *Nat. Rev. Genet.* 3, 662-673). Changes in DNA methylation leading to aberrant gene silencing have been demonstrated in several human cancers (reviewed, e.g., in Robertson, K. D. and Wolffe, A. P. (2000) *Nat. Rev. Genet.* 1, 11-19). Hypermethylation of promoters was demonstrated to be a frequent mechanism leading to the inactivation of tumor suppressor genes (Bird, A. P. (2002) *Genes Dev.* 16, 6-21).

Various methods exist for experimentally determining differential methylation in individual genes (reviewed, e.g., in Rein, T. et al. (1998) *Nucleic Acids Res.* 26, 2255-2264). These techniques include inter alia bisulfite sequencing, methylation specific PCR (MSP), Methylight and pyro-sequencing.

One common prerequisite for performing the above techniques is the bisulfite-mediated conversion (also referred to as bisulfite modification) of the DNA to be analyzed. In particular, unmethylated cytosine residues are converted into uridine residues. The three-step reaction scheme for the bisulfite-mediated conversion from cytosine to uracil is schematically shown in FIG. 1. In brief, cytosine is sulfonated to cytosine-bisulfite under slightly acidic conditions. Hydrolytic deamination to uracil-bisulfite occurs spontaneously. The latter one is then desulfonated to uracil under basic conditions.

Since methylated cytosine residues are not converted to uridine residues, during bisulfite treatment, the DNA sequence in unmethylated CpG islands is effectively changed (C to U), while methylated DNA retains its original sequence.

However, for a valid diagnostic results based on the analysis of the DNA methylation status it is desirable that the DNA is converted with maximal efficiency, that is, ideally 100% of the unmethylated cystosine residues present in a given DNA sequence are converted to uridine residues.

Bisulfite-mediated DNA conversion is typically performed using commercially available reaction kits. In these test systems, the DNA is often incubated for a long period of time (in many cases, overnight) at a comparably high reaction temperature (e.g., 60° C.). Repeated heating steps to 95° C. are necessary during this time of incubation in order to denature the DNA. In many cases, incubation time is supposed to reach the highest DNA conversion efficiency by simply letting the reaction run for as much time as seems adequate and/or is tolerable while maintaining a certain level of DNA quality. On the other hand, it is also apparent that prolonged heating periods finally result in the degradation of DNA, and thus in a decrease in DNA yield and integrity. This may be fatal for any downstream analyses, for example, if the DNA concentration in the sample is low.

However, different sample DNAs to be analyzed or different applications likely required distinct experimental set-ups in order to achieve maximal efficiency. For example, the use of a crude lysate with unpurified DNA poses more uncertainties than a purified sample DNA. In a crude lysate, other substances are present that may potentially interact with the bisulfite salt and thus interfere with the DNA conversion reaction.

In view of the above considerations it is evident that a general approach of "one incubation time fits all" is not reasonable since it would lead to an unnecessary loss of DNA quality due to prolonged heat exposure when DNA samples are analyzed that are easy to convert (e.g., purified DNA molecules). Vice versa, the DNA in complex samples (e.g., crude lysates, body fluids, frozen biopsies) may only be converted to a rather small extent, if at all.

Currently, no methods are available that actively monitor performance and progression of bisulfite-mediated DNA conversion. However, the provision of such a method would aid to accurately determine the endpoint (i.e. 100% completion) of each individual reaction, thus enabling to switch from a generalized protocol to sample-specific reaction conditions Unnecessary and excessive heat incubation times could be avoided, thereby improving DNA quality.

Hence, there remains a continuing need for a method allowing for an accurate monitoring of the bisulfite-mediated DNA conversion overcoming the above limitations. In particular, there is a need for a corresponding method enabling the setup of individualized reaction conditions for each sample DNA analyzed, thus improving the results of differential DNA methylation analyses

SUMMARY OF THE INVENTION

It is an objective of the present invention to provide novel approaches for monitoring the progression of the bisulfite-mediated conversion of DNA during DNA methylation analysis.

More specifically, it is an objective to provide a method allowing for the precise determination of the endpoint of the conversion.

Furthermore, it is an objective to provide a method enabling an accurate control as well as the matching of the reaction conditions applied to the specific requirements of a sample DNA employed, thus resulting in an overall improvement of the DNA quality obtained.

These objectives as well as others, which will become apparent from the ensuing description, are attained by the subject matter of the independent claims. Some of the preferred embodiments of the present invention are defined by the subject matter of the dependent claims.

In one aspect, the present invention relates to a method for monitoring the bisulfite-mediated conversion of DNA during DNA methylation analysis, comprising:
(a) providing a sample DNA to be analyzed and at least one DNA reporter molecule, wherein the at least one DNA reporter molecule comprises:
(i) in its nucleotide sequence at least one unmethylated cytosine residue; and
(ii) at least one label;
and wherein the sample DNA and the at least one DNA reporter molecule are provided in spatially separated reaction compartments that are in fluid connection with each other;
(b) adding a bisulfite salt to the spatially separated reaction compartments, thus mediating the conversion of the unmethylated cytosine residues comprised in the nucleotide sequences of the sample DNA and the at least one DNA reporter molecule into uridin residues;
(c) adding an uracil-DNA-glycosylase to the at least one DNA reporter molecule, thus mediating the removal of the uracil bases obtained in step (b) from the DNA backbone;
(d) fragmentation of the DNA obtained in step (c) by heat treatment; and
(e) detecting the at least one label released from the at least one synthetic DNA reporter molecule during step (d).
In one embodiment, the method further comprises:
(f) comparing the results obtained in (e) with a reference value.

In another embodiment, the detection step is repeated at least once within a given period of time.

Preferably, the results obtained in step (e) are used for controlling the progression of the reaction according to step (b).

In a preferred embodiment, the at least one DNA reporter molecule is a synthetic oligonucleotide. In specific preferred embodiments, the at least one synthetic DNA reporter molecule is immobilized on a support.

In another preferred embodiment, the uracil-DNA-glycosylase is thermostable.

In one specific embodiment, steps (c), (d), and (e) are performed in the same reaction compartment employed for providing the at least one DNA reporter molecule. In an alternative embodiment, any one or more of steps (c), (d), and (e) are performed in at least one further spatially separated reaction compartment that is/are in fluid connection with the reaction compartment employed for providing the at least one DNA reporter molecule.

In a further specific embodiment, at least any one, and preferably all reaction compartment(s) is/are provided with one or more temperature control units for controlling and regulating the temperature within the reaction compartment(s).

In a preferred embodiment, the spatial separation between reaction compartments is accomplished by means of a semi-permeable membrane, preferably a size exclusion membrane or a micro-dialysis membrane.

In a further preferred embodiment, the at least two spatially separated reaction compartments in fluid connection with each other are integrated into a sensor device, preferably a continuous sensor device.

In another aspect, the present invention relates to the use of a method as defined herein for analyzing the methylation status of a sample DNA. Preferably, the analysis of the DNA methylation status is performed for diagnosing cancer.

BRIEF DESCRIPTION OF THE DRAWINGS

FIG. 6 depicts a schematic representation of another embodiment of the method according to the present invention performed in an exemplary sensor device having at least two separated reaction compartments in fluid connection with each other. The one DNA reporter molecules employed are immobilized on the surface of one of the reaction compartments. Panel A illustrates the bisulfite-mediated conversion of sample DNA and the DNA reporter molecules. Panel B shows the addition of UNG from a reservoir at suitable temperature and buffer conditions. Panel C shows the heat-induced fragmentation of the "converted" DNA reporter molecules. A detailed description of this embodiment is given in example 4.

DETAILED DESCRIPTION

Figure 1:
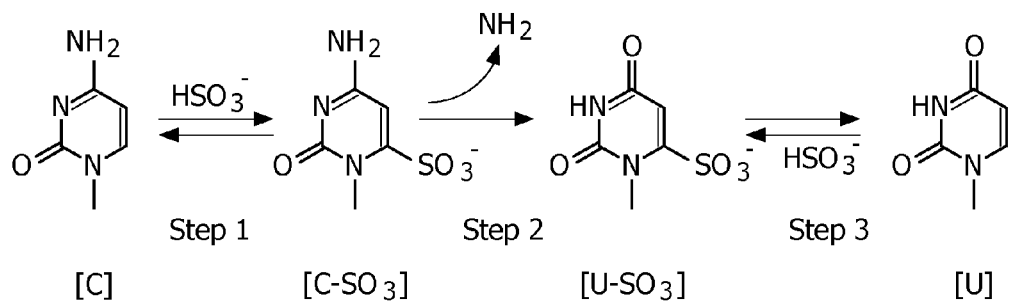
FIG. 1 schematically depicts the general three-step reaction scheme for the bisulfite-mediated conversion from cytosine (left) to uracil (right). Cytosine is sulfonated to cytosine-bisulfite under slightly acidic conditions. Hydrolytic deamination to uracil-bisulfite occurs spontaneously. The latter one is then desulfonated to uracil under basic conditions.

The present invention is based on the unexpected finding that by combining the reaction of the enzyme uracil-DNA-glycosylase (UNG) with at least one labeled DNA reporter molecule, the reporter molecule comprising at least one unmethylated cytosine residue in its sequence a versatile, accurate, and efficient method for monitoring the progression of the bisulfite-mediated conversion of DNA during DNA methylation analysis can be established.

The present invention illustratively described in the following may suitably be practiced in the absence of any element or elements, limitation or limitations, not specifically disclosed herein.

The present invention will be described with respect to particular embodiments and with reference to certain drawings but the invention is not limited thereto but only by the claims. The drawings described are only schematic and are to be considered non-limiting.

Where the term "comprising" is used in the present description and claims, it does not exclude other elements or steps. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun e.g. "a" or "an", "the", this includes a plural of that noun unless something else is specifically stated.

The term "about" in the context of the present invention denotes an interval of accuracy that the person skilled in the art will understand to still ensure the technical effect of the feature in question. The term typically indicates deviation from the indicated numerical value of ±10%, and preferably ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used.

The following terms or definitions are provided solely to aid in the understanding of the invention. These definitions should not be construed to have a scope less than understood by a person of ordinary skill in the art.

In one aspect, the present invention relates to a method for monitoring the bisulfite-mediated conversion of DNA during DNA methylation analysis, comprising:
(a) providing a sample DNA to be analyzed and at least one DNA reporter molecule, wherein the at least one DNA reporter molecule comprises:
 (i) in its nucleotide sequence at least one unmethylated cytosine residue; and
 (ii) at least one label;
 and wherein the sample DNA and the at least one DNA reporter molecule are provided in spatially separated reaction compartments that are in fluid connection with each other;
(b) adding a bisulfite salt to the spatially separated reaction compartments, thus mediating the conversion of the unmethylated cytosine residues comprised in the nucleotide sequences of the sample DNA and the at least one DNA reporter molecule into uridin residues;
(c) adding an uracil-DNA-glycosylase to the at least one DNA reporter molecule, thus mediating the removal of the uracil bases obtained in step (b) from the DNA backbone;
(d) fragmentation of the DNA obtained in step (c) by heat treatment; and
(e) detecting the at least one label released from the at least one synthetic DNA reporter molecule during step (d).

The term "sample DNA", as used herein, denotes any sample comprising one or more DNA molecules whose differential methylation status is to be analyzed once the unmethylated cytosine residues comprised in their nucleotide sequences are converted into uridine residues. The DNA molecules may be naturally occurring or synthetic compounds (e.g., generated by means of recombinant DNA technology or by chemical synthesis) and may be single-stranded or double-stranded. The DNA molecules may have any length. Typically, the length varies between 10 bp and 100000 bp, preferably between 100 bp and 10000 bp, and particularly preferably between 500 bp and 5000 bp.

The DNA molecules comprised in the sample DNA may be present in purified form (e.g., provided in a suitable buffer solution such as TE or PBS known in the art) or may be included in an unpurified, partially purified or enriched sample solution. Examples of such unpurified samples include crude cell lysates, body fluids (e.g., blood, serum, salvia, and urine), solubilized tissues, and the like.

In some embodiments, the method according to the present invention comprises the purification of the DNA present in such an unpurified sample. Purification is typically accomplished after completion of the bisulfite-mediated DNA conversion. Methods and corresponding devices for purifying DNA (optionally as integral part of an automated system or working platform) are well known in the art and commercially available from many suppliers.

The term "DNA reporter molecule", as used herein, refers to a DNA molecule that comprises in its nucleotide sequence at least one unmethylated cytosine residue and at least one label that is used as the actual substrate for monitoring the bisulfite-mediated DNA conversion resulting in the release of a detectable label. The method of the invention is performed with at least one DNA reporter molecule, that is, with one or more such molecules. In case, more than one DNA reporter molecules are employed, these are typically of the same type (i.e. having the same nucleic acid sequence and/or labels). However, it may also be possible to use DNA reporter molecules of different types (i.e. having different nucleic acid sequences and/or labels).

In general, the DNA reporter molecules used in the present invention are nucleic acid molecules having a length of 10 to 150 nucleotides, for example 15 to 80 nucleotides, 15 to 60 nucleotides or 15 to 40 nucleotides. The DNA reporter molecules may be naturally occurring molecules or, preferably, synthetic ones (e.g., generated by means of recombinant DNA technology or chemical synthesis). Preferably, the reporter molecules used in the invention are single-stranded nucleic acid molecules. However, double-stranded molecules may also be employed.

In a preferred embodiment, the at least one DNA reporter molecule is a synthetic oligonucleotide (i.e. single-stranded).

For performing the detection reaction, the DNA reporter molecule comprises one or more detectable labels. The term "label", as used herein, refers to any compound or moiety that comprises one or more appropriate chemical substances or enzymes, which directly or indirectly generate a detectable compound or signal in a chemical, physical or enzymatic reaction. As used herein, the term is to be understood to include both detectable labels as such as well as any compounds coupled to one or more such detectable markers. Furthermore, within the scope of the present invention, moieties interfering with the generation of a detectable signal by a label (e.g., a quencher "hijacking" the emissions that resulted from excitation of the fluorophor, as long the quencher and the fluorophor are in close proximity to each other) also belong to the labels. The labels may be incorporated or attached to the reporter molecules, e.g., in form of modified and/or labeled ribonucleotides, deoxynucleotides or dideoxynucleotides. The labels may be attached to the 5'-terminus and/or the 3'-terminus and/or any internal nucleotide within the sequence of a DNA reporter molecule.

Detectable labels that may be used according to the invention include any compound, which directly or indirectly generates a detectable compound or signal in a chemical, physical or enzymatic reaction. Labeling can be achieved by methods well known in the art (see, for example, Sambrook, J. et al. (1989) *Molecular, Cloning: A Laboratory Manual*, 2nd ed., Cold Spring Harbor Laboratory Press, Cold Spring Harbor, N.Y.; and Lottspeich, F., and Zorbas H. (1998) *Bioanalytik*, Spektrum Akademischer Verlag, Heidelberg/Berlin, Germany). The labels can be selected inter alia from fluorescent labels, enzyme labels, colored labels, chromogenic labels, luminescent labels, radioactive labels, haptens, biotin, metal complexes, metals, and colloidal gold. All these types of labels are well established in the art. An example of a physical reaction that is mediated by such labels is the emission of fluorescence or phosphorescence upon irradiation or excitation or the emission of X-rays when using a radioactive label. Alkaline phosphatase, horseradish peroxidase, β-galactosidase, and β-lactamase are examples of enzyme labels, which catalyze the formation of chromogenic reaction products, and which may be used in the invention. In specific preferred embodiments of the invention, the detectable labels are fluorescent labels. Numerous fluorescent labels are well established in the art and commercially available from different suppliers (see, for example, *The Handbook—A Guide to Fluorescent Probes and Labeling Technologies*, 10th ed. (2006), Molecular Probes, Invitrogen Corporation, Carlsbad, Calif., USA).

For detecting such labels, the device used for performing the method of the invention may comprise a detection system suitable for determining values indicative for the presence and/or amount of the labels. The selection of a suitable detection system depends on several parameters such as the type of labels used for detection or the kind of analysis performed. Various optical and non-optical detection systems are well established in the art. For example, fluorescence detection methods that may be used in the invention include inter alia fluorescence resonance energy transfer (FRET), bioluminescence resonance energy transfer (BRET), and fluorescence correlation spectroscopy.

In specific embodiments, detection is performed using FRET or BRET, which are based on the respective formation of fluorescence or bioluminescence quencher pairs. The use of FRET is also described, e.g., in Liu, B. et al. (2005) *Proc. Natl. Acad. Sci. USA* 102, 589-593. The use of BRET is detailed, for example, in Xu, Y. et al. (1999) *Proc. Natl. Acad. Sci. USA* 96, 151-156.

The at least one DNA reporter molecule may be provided in unbound form (i.e. free molecules in a solution). In specific embodiments, the DNA reporter molecules are immobilized on a support (i.e. attached to a matrix). Typically, the support is a solid member, e.g. a solid surface. Attachment of the DNA reporter molecules to the support may be accomplished by any direct (e.g., via an anchor group comprised in the reporter molecule) or indirect (for example, via capture molecules mediating the binding) interaction of the DNA reporter molecules with a given support member. This interaction may be a covalent or a non-covalent binding and is generally reversible. For example, carbodiimide chemistry can be used to covalently couple the DNA reporter molecules to activated surfaces. A suitable amine linker at the 5'- or 3'-terminus of the DNA reporter molecule is then provide for this purpose. Various other established chemistries for achieving the immobilization of the DNA reporter molecules are known in the art.

The DNA reporter molecules may be immobilized on a mobile support, preferably beads such as magnetic beads, polystyrene beads, and latex beads. Such a mobile support member can be transferred in the fluid flow of the sensor device used for performing the method.

On the other hand, it is also possible to directly immobilize the DNA reporter molecules on the inner surface of a reaction compartment or, e.g., on a microscope slides, wafer or a ceramic materials that are arranged in a reaction compartment but cannot be freely transferred.

In some embodiments, the results of the detection reaction are compared with a reference value, for example the value obtained with a fixed amount of label (e.g., provided as an internal control) or with data from the literature.

Preferably, the detection step is repeated at least once within a given period of time, for example 30 min, 60 min, 120 min, 6 h, 12 h, 24 h, 48 h, and the like. Multiple repetitions are possible, e.g., 2, 5, 8, 10, 15, 20, 30, and so forth. Repetitions may be performed in fixed time intervals over the given period of time. However, the time intervals between the repetitions may also vary, for example become shorter as the bisulfite-mediated DNA conversion reaches completion in order to precisely determine the endpoint of the reaction. In other words, the results obtained during detection are used for controlling the progression of the DNA conversion. If the bisulfite-mediated conversion of the at least one DNA reporter molecule is complete, it is considered that the same applies to the sample DNA.

Within the present invention, the sample DNA and the at least one DNA reporter molecule are provided in spatially separated reaction compartments that are in fluid connection with each other. That it, the sample DNA is provided in a first reaction compartment, and the at least one DNA reporter molecule is provided in a second reaction compartment, the two compartments representing separate entities. The term "reaction compartment" (also referred to as "reaction chamber"), as used herein, denotes any structure for accommodating liquid samples. Various configurations of such structures (e.g., having a cuboid or cylindrical three-dimensional shape) are well known in the art.

However, the reaction compartments are not self-contained but in fluid communication with each other, that is, at least a portion of the components may be transferred in the fluid flow between the compartments. This may be accomplished, e.g., by means of connecting the reaction compartments via microfluidic channels. In preferred embodiments, the spatial separation between the reaction compartments is accomplished by means of a semi-permeable membrane, preferably a size exclusion membrane or a micro-dialysis membrane. Such a semi-permeable membrane allows small molecules to pass the barrier, while larger ones (i.e. exceeding a given size limit depending on the properties of the membrane) are retained.

The addition of a bisulfite salt (e.g., sodium bisulfit but any other salt is suitable as well) to the spatially separated reaction compartments for mediating the conversion of the unmethylated cytosine residues comprised in the nucleotide sequences of the sample DNA and the at least one DNA reporter molecule into uridin residues is performed according to standard protocols known in the art. Reagents are also commercially available from different suppliers. The general reaction scheme is schematically depicted in FIG. 1. The DNA conversion is typically performed at a reaction temperature between 40-70° C., preferably between 55-65°, and particularly preferably at 60° C. The incubation period may vary (depending inter alia on the sample to be analyzed) between several minutes to several hours (e.g., over night) or even longer.

The DNA conversion of the sample DNA and the at least one DNA reporter molecules occurs in parallel (I.e. under the same experimental conditions) in spatially separated reaction compartments. The respective reagents required may be added from particular reservoirs to either one and/or both of the reaction compartment in which the respective DNA molecules are provided.

In order to adjust a particular reaction temperature at least any one, and preferably all reaction compartment(s) employed for carrying out the present invention is/are provided with one or more temperature control units for controlling and regulating the temperature within the reaction compartment(s). Such a temperature control unit may comprise one or more separate heating and/or cooling elements, which may directly contact one or more reaction compartments of the device used. Various heat control systems are well known in the art and available from different suppliers.

Figure 2:
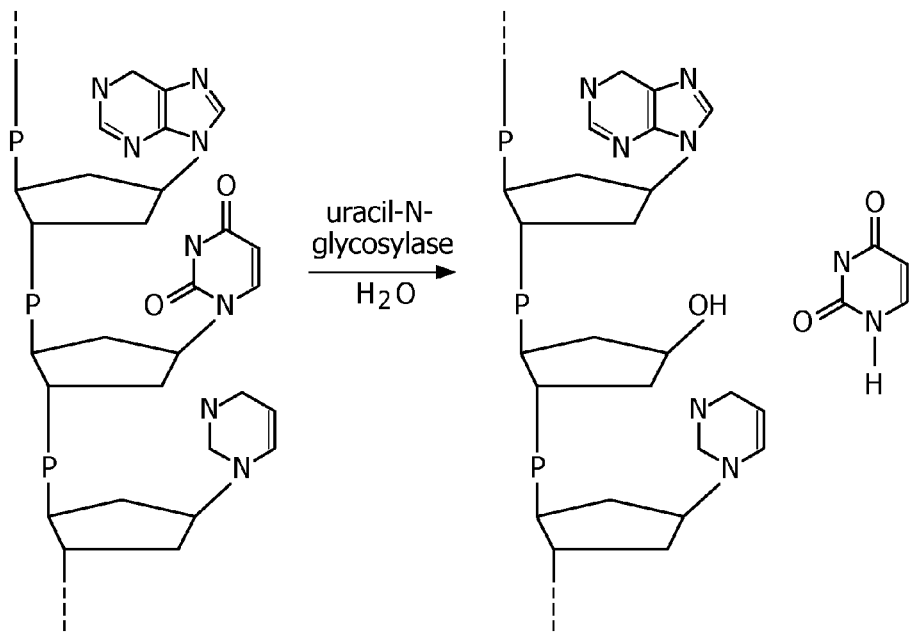
FIG. 2 schematically depicts the reaction of uracil-DNA-glycosylase (UNG) on uridine residues in a stretch of DNA. Uridine residues can only be found in DNA if cytosine is deaminated to uracil, leading to mutations in the DNA. UNG removes uracil bases from the sugar-phosphate backbone of the DNA. Although the DNA backbone remains intact, the resulting abasic sites are susceptible to hydrolytic cleavage at raised temperatures.

The enzyme uracil-DNA-glycosylase (UNG) is commonly used in PCR reactions to prevent a "carry-over" of potentially contaminating PCR products from previous reactions. It is commercially available from many suppliers and acts on single-stranded as well as on double-stranded DNA. UNG is part of the DNA repair apparatus of cells with the task of removing uridine residues. Uridine can only be found in DNA if cytosine is deaminated to uracil, leading to mutations in the DNA. The enzyme removes uracil bases from the sugar-phosphate backbone of DNA, a reaction schematically illustrated in FIG. 2. This reaction is part of the so-called base excision repair mechanism, preventing in this case cytosine deamination mutations in DNA.

Any known uracil-DNA-glycosylase may be employed in the present invention. The enzyme is added to the at least one DNA reporter molecule but not to the sample DNA. The enzymatic reaction (i.e. the removal of the uracil bases obtained during bisulfite-mediated conversion) from the DNA backbone occurs under established standard reaction conditions depending on the particular enzyme employed.

In preferred embodiments, a thermostable UNG enzyme is used, in particular an UNG enzyme derived from a thermophilic organism. Such thermostable UNG enzymes are known in the art (e.g. Sartori, A. A. et al (2001) *J. Biol. Chem.* 276, 29979-29986; Sartori, A. A. et al (2002) *EMBO J.* 21, 3182-3191). They maintain a high activity even at temperatures of more than 90° C.

The UNG-mediated enzymatic reaction may be performed in the same reaction compartment in which the at least one DNA reporter molecule has been provided or in a further (i.e. third) reaction compartment that is spatially separated but in fluid communication with the one in which the at least one DNA reporter molecule has been provided. The necessary reagents may be provided from specific reservoirs in fluid communication with the respective reaction compartment.

The DNA reporter molecules obtained after the UNG-treatment still have an intact DNA backbone but one or more abasic sites where uracil bases have been removed. These abasic sites are susceptible to hydrolytic cleavage at raised temperatures, e.g. temperatures between 90° C. and 95° C.

Within the present invention the heat-induced fragmentation may be performed for various time periods, for example 10 s, 30 s, 1 min, 2 min, 5 min, depending on the type and amount of DNA present. The person of skill in the art is well aware how to select the incubation time.

The heat-induced fragmentation step may be performed in the same reaction compartment in which the at least one DNA reporter molecule is provided (and in which optionally also the UNG-mediated reaction took place) or in another spatially separated reaction compartment. The latter one may be the same reaction compartment in which the UNG-mediated reaction took place (i.e. the third one) or a further (i.e. fourth) one that is spatially separated but in fluid communication with the second one and/or the third one.

Finally, the detection step may be performed in the same reaction compartment in which the at least one DNA reporter molecule is provided (and in which optionally also the UNG-mediated reaction and the heat-induced fragmentation took place) or in another spatially separated reaction compartment. The latter one may be the third one or the fourth one already described above or it may be a further (i.e. fifth) one that is spatially separated but in fluid communication with the second one and/or the third one and/or the fourth one.

Figure 3:
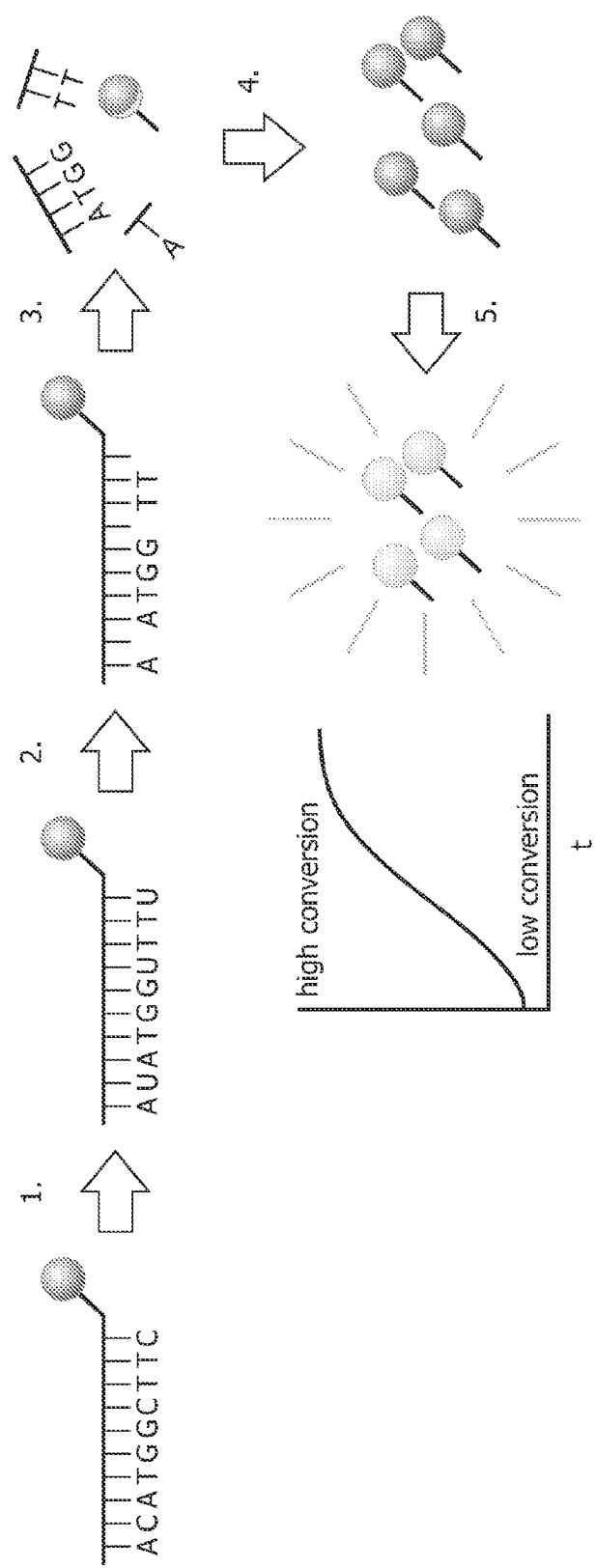
FIG. 3 schematically depicts the principle of the method according to the present invention. Provided is at least one labeled DNA reporter molecule comprising in its nucleotide sequence unmethylated cytosine residues that are converted into uridine residues by means of adding a bisulphate salt (1.). Treatment of the DNA with UNG results in the removal of the uracil bases from the DNA backbone (2.), thus making it susceptible to heat-induced fragmentation at these abasic sites (3.). The labels released from the at least one DNA reporter molecule are optionally separated (4.) and detected by an appropriate analysis method.

The principle of the method according to the present invention is schematically summarized in FIG. 3.

In some embodiments, the at least two spatially separated reaction compartments in fluid connection with each other are integrated into a sensor device, preferably a continuous sensor device. The sensor device may, in turn, be an integral part of an automated platform or working station also including, e.g., means for DNA sample purification and/or for subsequent analyses of differential methylation (for example, a thermal cycler for performing PCR reactions). Such platforms are known in the art and commercially available.

In another aspect, the present invention relates to the use of a method as defined herein for analyzing the methylation status of a sample DNA. In other words, the present method for monitoring the progression of the bisulfite-mediated DNA conversion is a prerequisite for ensuring accuracy and reliability of downstream applications by providing high quality (i.e. fully converted) DNA. Such downstream applications include bisulfite-sequencing, methylation-sensitive single-strand conformation analysis (MS-SSCA), methylation-sensitive single nucleotide primer extension (MS-SnuPE), methylation-sensitive microarray applications, combined bisulfite restriction analysis (COBRA), methlyation-sensitive real-time PCR applications, and the like.

In preferred embodiments, the analysis of the DNA methylation status is used for diagnosing cancer.

The invention is further described by the figures and the following examples, which are solely for the purpose of illustrating specific embodiments of this invention, and are not to be construed as limiting the scope of the invention in any way.

EXAMPLES

Example 1

Monitoring Bisulfite-Mediated DNA Conversion in a Continuous Sensor Device

Figure 4:
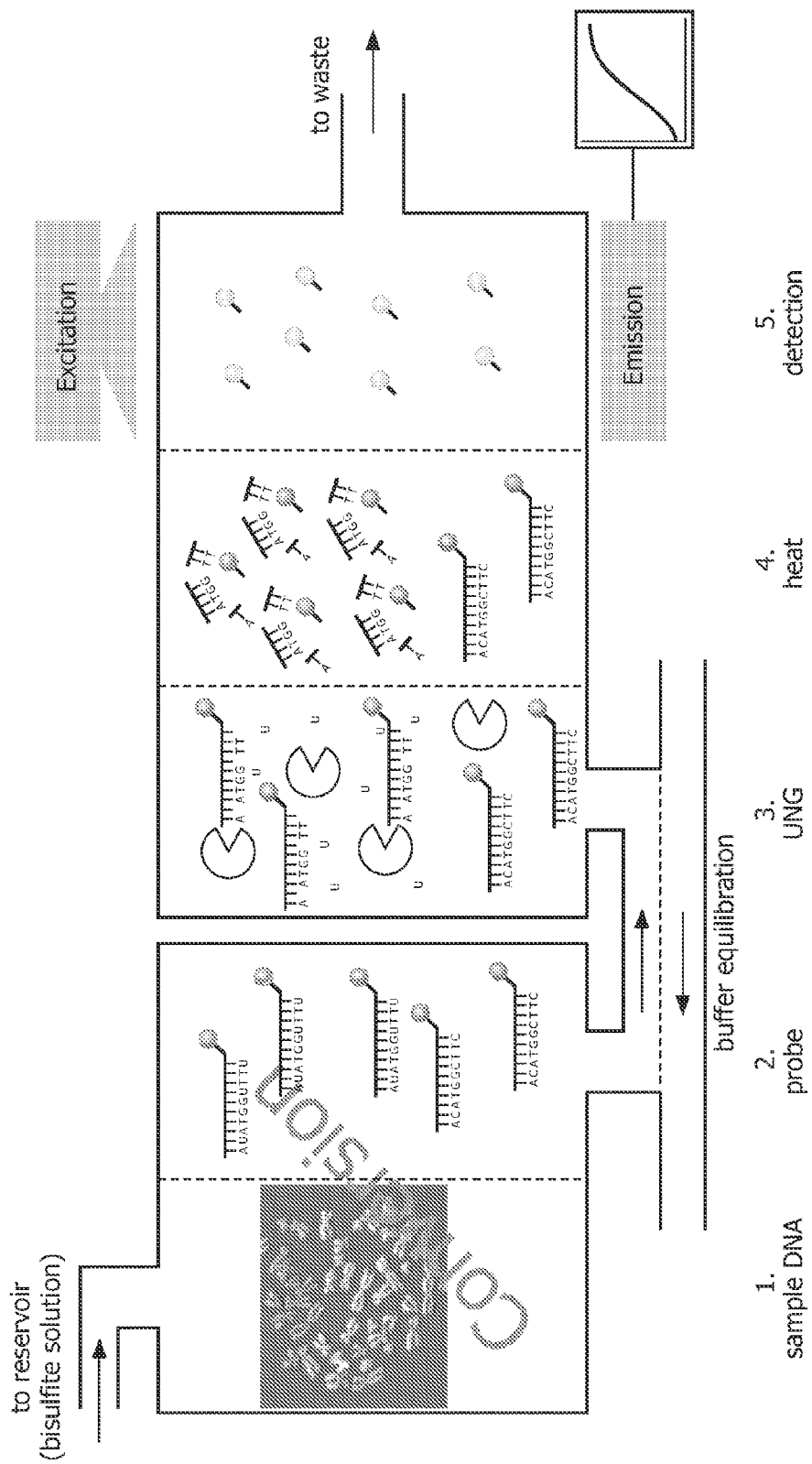
FIG. 4 depicts a schematic representation of one embodiment of the method according to the present invention performed in an exemplary sensor device having at least five spatially separated reaction compartments in fluid connection with each other. A detailed description of this embodiment is given in example 1.
Figure 5A:
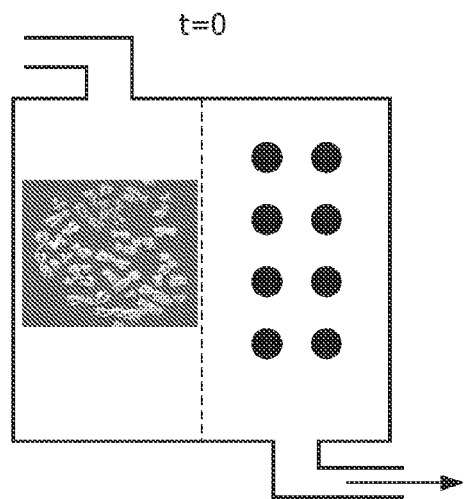
FIG. 5 schematically depicts the collection of discrete data points by using fractions of DNA reporter molecules immobilized on a solid support (i.e. the surface of beads) in an exemplary sensor device having at least two spatially separated reaction compartments in fluid connection with each other. Panels A-C illustrate a schematic time series of fractional release. Panel D represents a possible plot for determining the efficiency of DNA conversion. Details are given in example 3.
Figure 5B:
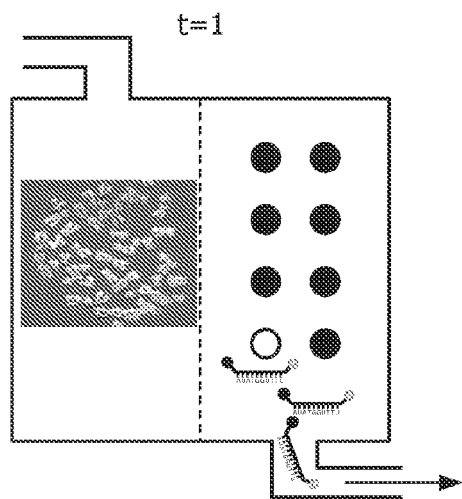
Figure 5C:
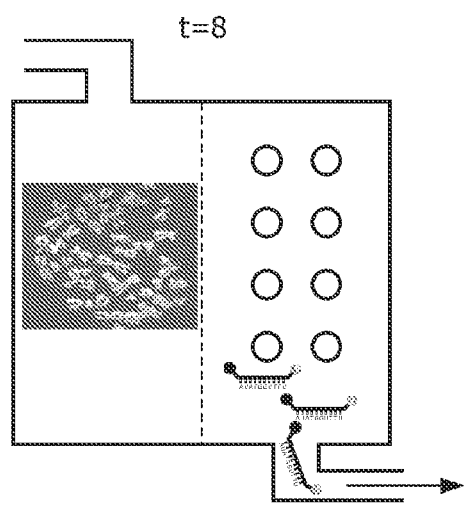
Figure 5D:
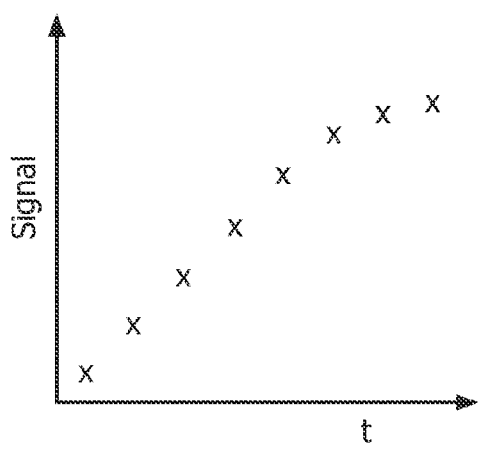

In this embodiment, the method according to the present invention is performed in an exemplary continuous sensor that is schematically illustrated in FIG. 4.

In such a scenario, it is desirable that the different steps of the method take place in different spatially separated reaction compartments. This configuration of the sensor device prevents interference between different method steps and incompatibilities between reaction components. For example, the enzymatic activity of uracil-DNA-glycosylase (UNG) may significantly decrease during the heat fragmentation step.

The sensor device shown in FIG. 4 has at least five spatially separated reaction compartments. In a first reaction compartment, the sample DNA is provided. The sample DNA may be removed from this compartment for subsequent analyses of the methylation status (not shown). The first compartment is connected to a suitable amount of reservoirs, containing the necessary components for the preparation and conversion of DNA (e.g. the bisulfite solution).

The first reaction compartment is located immediately adjacent to a second reaction compartment in which the at least one DNA reporter molecule (i.e. a labeled synthetic DNA oligonucleotide).

The spatial separation between the two reaction compartments is accomplished in a manner such that the conversion reagents can pass, but the sample DNA is retained in the first chamber, that is, via a semi-permeable barrier, e.g. by means of a size exclusion (filter) membrane. In other words, the two reaction compartments are in fluid communication with each other.

The temperature in the first and the second reaction compartments can be controlled allowing for the adjustment of suitable reaction conditions (e.g., 60° C.) by employing one or more heating (and/or cooling) elements.

In a third reaction compartment, the UNG enzyme is provided and the removal of the uracil bases from the "converted" at least one DNA reporter molecule takes place. The spatial separation between the second and third reaction compartments is accomplished in such a manner that buffer components can be replaced or removed, e.g. by means of a microdialysis membrane, to generate optimal reaction conditions for the UNG enzyme.

In a fourth reaction compartment that is located adjacent to the third one, the heat-induced hydrolytic cleavage of the DNA reporter molecule at the abasic sites takes place. The spatial separation between the third and fourth reaction compartments is configured in such a manner that the UNG enzyme molecules are retained but not the DNA reporter molecules, e.g., by means of a (semi-permeable) size exclusion (filter) membrane.

In a fifth reaction compartment that is located adjacent to the fourth one, detection of the labels (e.g., a fluorescent dye) released during the previous fragmentation step takes place. The spatial separation between the fourth and fifth reaction compartments is configured in such a manner that the labels and fragmented DNA reporter molecules can pass to the fifth reaction compartment but any intact DNA reporter molecules are retained in the fourth reaction compartment, e.g. by means of a (semi-permeable) size exclusion (filter) membrane.

The amount of the at least one DNA reporter molecule provided in the second reaction compartment at the start of the reaction scheme is preferably such that the fraction entering the subsequent reaction pathway may be considered constant over the time of the assay. The detected amount of label is then a measure for the conversion of DNA.

The signal generated by the labels is normalized to the fraction of DNA reporter molecules that enters the third reaction compartment, e.g. determined by means of a UV measurement of the nucleic acid content.

The fraction of DNA reporter molecules that are not converted and thus not fragmented by the combined action of UNG and heat are re-directed back to the second reaction compartment. Then, these DNA reporter molecules enter the conversion reaction again. This can be accomplished, e.g., by means of a connection between the fourth and second reaction compartments (closed loop structure, not shown in FIG. 4).

Conventional microfluidics may be used to limit liquid and reagent amounts and to actuate the system.

Example 2

Use of Twofold Labeled DNA Reporter Molecules

In a further embodiment of the method according to the invention, the at least one DNA reporter molecule (i.e. a synthetic oligonucleotide) comprises a first and a second label.

The first label is a fluorescent dye that can be chosen from a variety of commercially available dyes. The second label is a suitable quencher for this dye. Alternatively, the second molecule is another fluorescent dye that forms together with the first dye a donor-acceptor pair for fluorescence resonance energy transfer (FRET).

Upon heat-induced fragmentation of the DNA reporter molecules the first fluorescent dye is separated from the quencher molecule. Alternatively, the FRET donor-acceptor pair is separated from each other. A fluorescence signal is then already detectable in the heat-induced fragmentation step.

Hence, by combining the fragmentation and detection steps one of the at least five reaction compartments of the sensor device illustrated in FIG. 4 is dispensable resulting in a simplified configuration of the device.

Example 3

Use of DNA Reporter Molecules Immobilized on Beads

For some applications, it may be preferable to generate only a few data points, e.g. to limit the amount of reagents, energy consumption, etc. In such a scenario, the at least one DNA reporter molecule (i.e. a synthetic oligonucleotide) comprises a suitable label attached to one terminus, e.g. the 3'-end, and is immobilized via the other terminus, e.g. the 5'-end, on a mobile surface, preferably a bead, such as a polystyrene bead or a magnetic bead.

In one specific embodiment, the beads are retained in the second reaction compartment of an exemplary sensor device and at certain time points a fraction of the beads might be released to enter the further compartment(s).

The collection of discrete data points by using fractions of DNA reporter molecules immobilized on a solid support (i.e. the surface of beads) in an exemplary sensor device having two spatially separated reaction compartments is schematically shown in FIG. 5. Panels A-C illustrate a schematic time series of fractional release. Panel D represents a possible plot for determining the efficiency of DNA conversion.

The use of DNA reporter molecules immobilized on beads in the second reaction compartment also enables the exchange of solutions in this compartment, while the DNA reporter molecules are retained. The requirement of buffer equilibration between the second and third reaction compartments of the sensor device shown in FIG. 5 is thus dispensable and can be omitted.

Furthermore, the fractional release of the DNA reporter molecules from the second reaction compartment allows for a more accurate control of the absolute number of DNA reporter molecules transferred to the further reaction compartment(s) (since the number of DNA reporter molecules per bead and the number of beads per release are known). This, in turn, facilitates the calculation of the ratio of unconverted/converted DNA reporter molecules.

Restricting the beads in the second reaction compartment may be accomplished, e.g., by using magnetic beads in conjunction with the application of magnetic fields or by using polystyrene beads in conjunction with electric AC fields and dielectrophoretic forces.

Example 4

Use of DNA Reporter Molecules Immobilized on the Inner Surface of a Reaction Compartment In a further embodiment, a sensor device comprising a first and a second reaction compartment is employed for performing the method of the present invention. The sensor device is schematically illustrated in FIG. 6.

The first reaction compartment (in which the sample DNA is provided) is connected to a reservoir containing the reagents required for bisulfite conversion.

The second reaction compartment is connected to at least one reservoir containing the UNG enzyme in a suitable buffer. The at least one DNA reporter molecule (i.e. a labeled synthetic oligonucleotide) is immobilized on the inner surface of the second reaction compartment, e.g., by using carbodiimide chemistry and an amino-linker at one terminus of the DNA reporter molecules. The other terminus of the DNA reporter molecule is modified with a suitable label, e.g., a fluorescent dye.

The first and second reaction compartments are spatially separated but in fluid communication with each other such that the exchange of buffer and/or conversion reagent is allowed but the sample DNA and enzymes cannot pass, e.g. by means of a semi-permeable size exclusion filter membrane.

The temperature in both reaction compartments can be adjusted to a level allowing for an efficient bisulfite-mediated DNA conversion. However, the temperature in the second reaction compartment can be regulated independently from that in the first reaction compartment, e.g. by using a second heating (and/or cooling) element.

In the first method step, the buffer conditions and the temperature in both reaction compartments are suitable for converting the sample DNA and the immobilized DNA reporter molecules (FIG. 6A).

In the second step, the temperature in the second reaction compartment is reduced enabling the UNG reaction to take place, e.g. 37° C. Then, the UNG enzyme from the reservoir is applied to the second compartment (FIG. 6B).

In the third step, the temperature in the second reaction compartment is raised, e.g. to 95° C., in order to fragment the DNA reporter molecules at the abasic sites (FIG. 6C). The labels released from the fragmented DNA reporter molecules are then measured via an appropriate detector. Alternatively, the labels of the still intact DNA reporter molecules at the surface may be measured, e.g., by using a fluorescence label in conjunction with TIRF, a confocal scanner, etc.

After heat treatment in the second reaction compartment the temperature is lowered again to the temperature of the first reaction compartment in order to continue the conversion reaction. At certain time points, the protocol is repeated, resulting in a discrete plot expressing the conversion efficiency over time (similar to FIG. 6D).

During UNG treatment, heat-induced fragmentation and label detection in the second compartment, the temperature in the first compartment is typically lowered to stop the conversion of the sample DNA. This allows for a better correlation of the conversion reactions obtained in the two compartments. Thus, in this embodiment discontinuous measurements are taken and a more sophisticated temperature control is necessary, but the complexity and the number of necessary compartments is reduced.

Example 5

Use of a Thermostable Uracil-DNA-Glycosylase (UNG)

In another embodiment of the method according to the present invention, a thermostable UNG enzyme is used, that remains active during the heat fragmentation. Preferably, however, UNG enzymes are used, that have been derived from thermophilic organisms. Such thermostable UNG enzymes are known in the art (e.g. Sartori, A. A. et al (2001) *J. Biol. Chem.* 276, 29979-29986; Sartori, A. A. et al (2002) *EMBO J.* 21, 3182-3191). They maintain a high activity even at temperatures of more than 90° C. The fragmentation step in the sensor device is performed at temperatures between 90° C. and 95° C. Thus, thermostable UNG enzymes remain active during and after the heat-induced fragmentation.

Figure 7A:
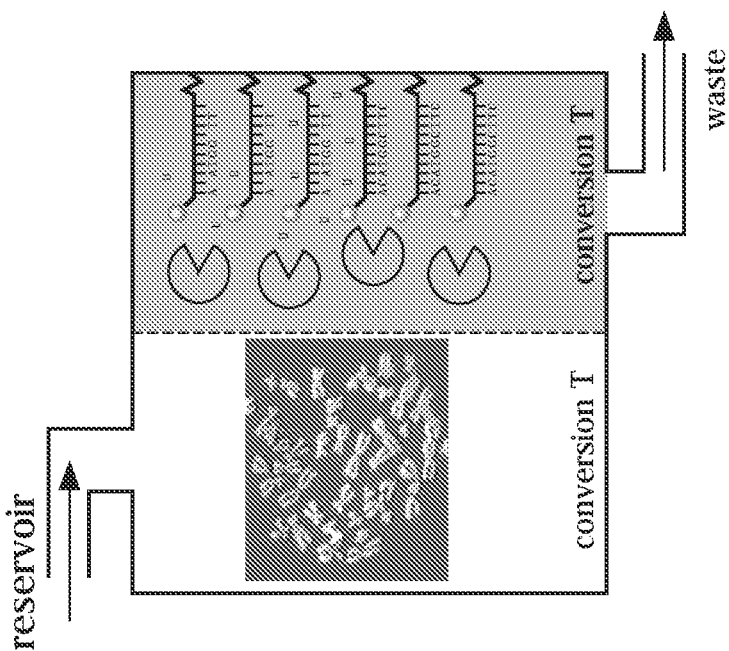
FIG. 7 depicts a schematic representation of a further embodiment of the method according to the present invention performed in an exemplary sensor device having at least two separated reaction compartments in fluid connection with each other. The UNG enzyme used is thermostable and thus can be provided together with the at least one DNA reporter molecules that are immobilized on the surface of one of the reaction compartments. A detailed description of this embodiment is given in example 5.
Figure 7B:
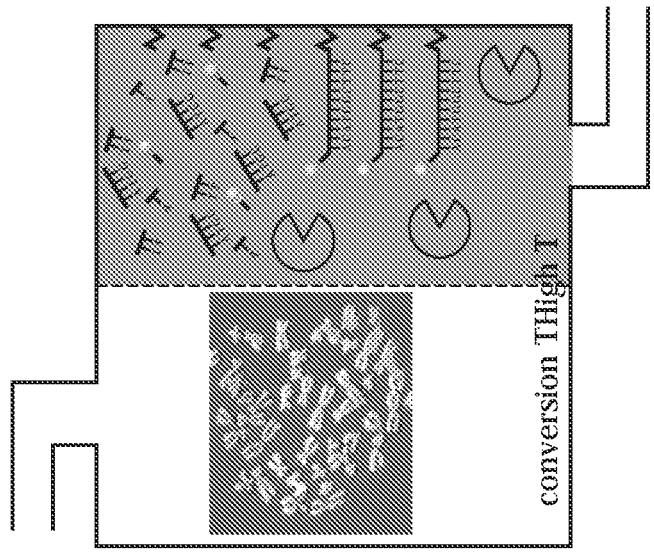

In this embodiment, the UNG enzyme is provided in the second reaction compartment together with the DNA reporter molecules (i.e. a labeled synthetic oligonucleotide) that are immobilized at the inner surface of the compartment. A two-compartment sensor device without enzyme reservoir is then sufficient, together with a two-step temperature protocol in the second reaction compartment. Both compartments are connected again by means of a semi-permeable size exclusion filter membrane in order to prevent the exchange of enzyme and sample DNA between the reaction compartments. An illustration of the sensor device employed is given in FIG. 7. Detection may be performed as described in examples 1-5 above.

Example 6

Sample DNA Purification

In order to further analyze the sample DNA after bisulfite-mediated conversion, e.g., by methylation-specific PCR or any other suitable technique, the sample DNA has to be provided in purified form.

Thus, for example, means and reagents for binding the DNA to a silica membrane with a suitable binding buffer (e.g., having a high content of a chaotropic salt), washing the bound DNA with a suitable buffer (e.g., having a high content of ethanol), and eluting the DNA with a suitable buffer (e.g., water or a buffered solution thereof) may be included in the method according to the present invention. This may be achieved by providing an outlet attached to the first reaction compartment, the outlet containing said silica membrane, and reservoirs for the respective reagent solutions.

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. Method for monitoring the bisulfite-mediated conversion of DNA during DNA methylation analysis, comprising:
    (a) providing a sample DNA to be analyzed and at least one DNA reporter molecule, wherein the at least one DNA reporter molecule comprises:
        (i) in its nucleotide sequence at least one unmethylated cytosine residue; and
        (ii) at least one label;
    and wherein the sample DNA and the at least one DNA reporter molecule are provided in spatially separated reaction compartments that are in fluid connection with each other;
    (b) adding a bisulfite salt to the spatially separated reaction compartments, thus mediating the conversion of the unmethylated cytosine residues comprised in the nucleotide sequences of the sample DNA and the at least one DNA reporter molecule into uridine residues;
    (c) adding an uracil-DNA-glycosylase to the at least one DNA reporter molecule, thus mediating the removal of the uracil bases obtained in step (b) from the DNA backbone;
    (d) fragmentation of the DNA obtained in step (c) by heat treatment; and
    (e) detecting the at least one label released from the at least one DNA reporter molecule during step (d).

2. The method of claim 1, further comprising: (f) comparing the results obtained in (e) with a reference value.

3. The method of claim 1, wherein the detection step is repeated at least once within a given period of time.

4. The method of claim 1, wherein the results obtained in step (e) are used for controlling the progression of the reaction according to step (b).

5. The method of claim 1, wherein the at least one DNA reporter molecule is a synthetic oligonucleotide.

6. The method of claim 1, wherein the at least one DNA reporter molecule is immobilized on a support.

7. The method of claim 1, wherein the uracil-DNA-glycosylase is thermostable.

8. The method of claim 1, wherein steps (c), (d), and (e) are performed in the same reaction compartment employed for providing the at least one DNA reporter molecule.

9. The method of claim 1, wherein any one or more of steps (c), (d), and (e) are performed in at least one further spatially separated reaction compartment that is/are in fluid connection with the reaction compartment employed for providing the at least one DNA reporter molecule.

10. The method of claim 1, wherein at least any one, and preferably all reaction compartment(s) is/are provided with one or more temperature control units for controlling and regulating the temperature within the reaction compartment(s).

11. The method of claim 1, wherein the spatial separation between reaction compartments is accomplished by means of a semi-permeable membrane.

12. The method of claim 11, wherein the semi-permeable membrane is comprised of a size exclusion membrane or a micro-dialysis membrane.

13. The method of claim 1, wherein the at least two spatially separated reaction compartments in fluid connection with each other are integrated into a sensor device.

14. The method of claim 13, wherein the sensor device is a continuous sensor device.

15. A method for analyzing the methylation status of a sample DNA which comprises the step of utilizing the method as defined in claim 1.

16. A method for diagnosing cancer which comprises the step of utilizing the method as defined in claim 1 for analyzing the methylation status of a sample DNA.

* * * * *